United States Patent [19]
Braithwaite

[11] Patent Number: 5,437,270
[45] Date of Patent: Aug. 1, 1995

[54] POWDER INHALER HAVING A MULTI-POSITIONED METERING CUP

[75] Inventor: Philip W. Braithwaite, Worcester, United Kingdom

[73] Assignee: Innovata Biomed Limited, St. Albans, England

[21] Appl. No.: 24,721

[22] Filed: Jan. 6, 1993

[30] Foreign Application Priority Data

Jul. 13, 1990 [GB] United Kingdom ................. 9015522

[51] Int. Cl.[6] .................... A61M 15/08; A61M 16/00; B05D 7/14; B65D 83/06
[52] U.S. Cl. .......................... 128/203.15; 128/203.19; 128/203.23
[58] Field of Search ...................... 128/203.15, 203.21, 128/203.12, 203.19, 203.23; 604/58

[56] References Cited

U.S. PATENT DOCUMENTS

| | | | |
|---|---|---|---|
| 2,587,215 | 2/1952 | Priestly | 128/203.15 |
| 4,200,099 | 4/1980 | Guenzel et al. | 222/362 |
| 4,274,403 | 6/1981 | Struve | 128/203.15 |
| 4,524,769 | 6/1985 | Wetterlin | 128/203.15 |
| 4,570,630 | 2/1986 | Elliott et al. | 128/203.15 |
| 4,668,218 | 5/1987 | Virtanen | 604/58 |

FOREIGN PATENT DOCUMENTS

| | | | |
|---|---|---|---|
| 3908 | 3/1911 | United Kingdom | 128/203.15 |
| 2041763 | 9/1980 | United Kingdom | 128/203.15 |

Primary Examiner—Kimberly L. Asher
Attorney, Agent, or Firm—Nixon & Vanderhye

[57] ABSTRACT

The inhaler includes a storage chamber for the powder to be delivered and an inhalation passage through which air is drawn via a mouth piece. A metering member having a frusto-conical side wall presents each dose to the inhalation passage in an upwardly open metering cup to be drawn therefrom by the air flow through the passage. A wiping element removed any particles of powder from the dispensing cup as it travels from the inhalation passage to the storage chamber to be refilled, and a chamber containing a moisture-absorbent material dries the empty cup and also dries the powder in the cup prior to inhalation to aid its removal from the cup. A mechanical counter is indexed each time the metering member is indexed to display the number of doses used or remaining.

12 Claims, 4 Drawing Sheets

POWDER INHALER HAVING A MULTI-POSITIONED METERING CUP

This is a continuation of PCT application No. PCT/GB91/01147, filed Jul. 11, 1991.

TECHNICAL FIELD OF THE INVENTION

This invention relates to an inhaler, namely a device for use in delivering a dose of medicament or other substance for inhaling into the lungs.

BACKGROUND

The most common form of inhaler propels the dose of medicament in pressurised gas from an aerosol. However, this form of inhaler is becoming less popular because of environmental and other considerations. The delivery of some drugs in a dry, finely divided form has been shown to have certain medical advantages over other forms of delivery.

Some known proposals for delivering medicament in a finely divided form cannot be operated by one hand. It is considered that one-handed operation should be an important feature of such an inhaler.

EP 079478, EP 166294 and GB 2165159 all disclose dry powder inhalers which can be operated by one hand. In each of these proposals the inhaler includes a medicament storage chamber and an inhalation passage through which air is drawn via a mouthpiece. A metering member provided with a metering recess transfers a dose of medicament from the storage chamber and deposits it in the inhalation chamber. It is considered that the accuracy of such an arrangement can be very poor: on the one hand, by repeated indexing of the metering member it is possible to deposit two or more doses of medicament into the inhalation passage resulting in the administration of an overdose of medicament; on the other hand, since the medicament normally drops from the metering recess into the inhalation passage under gravity, particles of medicament can adhere to the interior of the metering recess so that an underdose is delivered.

U.S. Pat. No. 2,587,215 also discloses dry powder inhalers with the same disadvantages as those mentioned above. However, this document also discloses an embodiment in which the metering member presents the medicament in an upwardly open dispensing cup to a mixing chamber where it is mixed with air before being sucked into an inhalation tube via a nozzle having a narrow opening. Air sucked into the inhaler passes into the inhalation tube either directly or through the mixing chamber and nozzle. Accordingly, not all the air passes over the dispensing cup. If medicament adheres to the surface of the dispensing cup but is not sucked therefrom, there will be an underdose of medicament delivered to the user. It is considered that, upon repeated use of the hollows to deliver doses to the inhalation passage, a continually increasing amount of the powder will adhere to the base of the hollow, resulting in progressively decreased dosage to the patient. The tendency for a build-up of adherent powder to occur is thought to be a source of inaccurate dosing in many of the inhalers previously proposed. The metering member is a rotary sliding device journalled on a cylindrical pivot member extending from the bottom of the body of the device. Such an arrangement is susceptible to jamming due to ingress of powder between the cylindrical contacting surfaces of the pivot member and the metering member.

Another form of inhaler which is currently available includes a metering member including a number of tapered metering recesses which are open at top and bottom. In use, finely divided medicament from a storage chamber is packed into the recesses whereupon the metering member is moved to a dispensing position in which air can be drawn through the recesses to draw out the medicament. This device is considered to have a number of major shortcomings. Firstly, the metering recesses are prone to clogging. Secondly, a large amount of suction is required so that the device is unsuitable for many patients with breathing problems. Thirdly, two hands are required to operate the device.

The aim of the present invention may be viewed as being to provide a form of inhaler for one-handed operation which is capable of administering accurate doses and avoids the risk of multiple dosing. A further aim is to provide an inhaler which does not require a large amount of suction for effective operation.

SUMMARY OF THE INVENTION

The present invention provides an inhaler for delivering a substance in a finely divided form, comprising a body defining a storage chamber for the substance to be delivered and further defining an inhalation passage through which air is drawn via a mouthpiece; a metering member operable to transfer a volumetric dose of the substance from the storage chamber to the inhalation passage, the metering member having a metering surface which is indented to provide at least one dispensing cup and being moveable between a first position in which a dispensing cup is presented to the storage chamber to receive a dose of the substance and a second position in which a dose of the substance is presented to the inhalation passage in a dispensing cup which is upwardly open in use; and cup clearing means for ensuring that the or each dispensing cup is substantially free from the substance before being presented to the storage chamber, the cup clearing means comprising means for moving the or each dispensing cup into a position from which, in normal use of the inhaler, any of the substance remaining in the dispensing cup would tend to fall, under the influence of gravity, out of the cup, after a dose of the substance has been presented in the cup to the inhalation passage and before that cup is again presented to the storage chamber.

Thus, in normal use of the inhaler repeated indexing of the metering member will not deposit multiple doses of the substance into the inhalation passage. Furthermore, removal of the substance from the metering member by the inhaled air flow rather than under gravity can ensure that the dose is more thoroughly removed.

The cup clearing means may comprise an inhalation passage so formed that the dose of the substance presented to the inhalation passage is subjected to substantially the entire airflow through the inhalation passage when air is drawn through the mouthpiece. Accordingly, whether air is drawn into the inhaler through a single opening or through several openings, the airflow through the device is such that all the air flows along a single duct at the point where the dispensing cup is presented to the airflow within this duct.

The cup clearing means may additionally consist of or comprise resilient wiping means for dislodging any residual substance from the or each cup after a dose of the substance has been presented therein to the inhalation passage and before that cup is again presented to the storage chamber. The provision of such dislodging means ensures that the or each dispensing cup is cleaned prior to refilling, and thereby prevents a build-up of adherent material with repeated refills.

Preferably, the metering member is resiliently biased into contact with a seat and is moveable while in contact with the seat. More preferably, the metering member is rotatable while in contact with the seat.

The metering member may comprise a frusto-conical side wall containing the dispensing cup or cups. Such a side wall can include a plurality of spaced-apart dispensing cups. The use of the frusto-conical shape in the wall of the metering member containing the dispensing cups allows a good seal to be obtained between the metering member and a seat against which the frusto-conical wall mates. Accordingly, either rigid or semi-rigid plastics materials can be used, and the appropriate shapes can be manufactured with relatively undemanding tolerances. Other shapes, such as spherical or cylindrical shapes, either demand much tighter tolerances in order to achieve the sort of seal required or resilient materials would have to be used or, possibly, an additional resilient sealing ring would have to be incorporated. The good seal referred to above should be such that the integrity of the stored drug is maintained by, for instance, preventing any ingress of moisture and/or contaminating air into the storage chamber.

The frusto-conical shape also makes it possible to form the metering member in such manner that it occupies relatively little space, so that the inhalation passage can be shorter than in many prior inhalers, reducing the amount of suction required from the patient.

Preferably, the longitudinal axis of the frusto-conical wall lies, when the inhaler is held in its normal in-use position, between vertical and an angle of 60° to the vertical. More preferably, this axis lies at an angle of about 45° to the vertical.

The body of the inhaler preferably comprises a seat having an annular contact surface making sliding contact with the motoring surface, the contact surface being frusto-conical in shape so as to define a socket within which the metering member is journalled for rotation between its first and second positions. The inhaler then preferably comprises means operable to resiliently bias the metering member into contact with the seat.

Preferably, an inhaler in accordance with the present invention includes a chamber for containing moisture-absorbent material, with which chamber the or each dispensing cup is moveable into register after a dose of the substance has been presented to the inhalation passage and before that cup is again presented to the storage chamber. In this way, the empty cup can be dried prior to filling to reduce adhesion of the surface in the cup. The filled dispensing cup may also move into register with the same or another chamber for moisture-absorbent material as it travels from the storage chamber to the inhalation passage. This could assist in preventing migration of moisture from the inhalation passage into the storage chamber.

The inhaler preferably includes display means which is indexed in association with the metering member to display an item of information to the user. The display means may comprise counter means for counting the number of times which a dispensing cup has been presented to the inhalation passage, and/or the number of doses remaining to be so presented.

As has been mentioned above, the provision of a frusto-conical shaped metering member is particularly advantageous in allowing greater manufacturing tolerances than would be possible with other configurations. If the metering member has a flat metering surface, as is the case in the above-described embodiment of U.S. Pat. No. 2,587,215, then it is necessary to provide a separate axle or spigot journalled on a part of the device. Such a separate axle is susceptible to jamming by the ingress of powder between the contacting surfaces associated with the axle.

Having regard to this, another aspect of the present invention provides an inhaler for delivering a substance in a finely divided form, comprising a body defining a storage chamber for the substance to be delivered and further defining an inhalation passage through which air is inhaled in use; and a metering member operable to transfer a volumetric dose of the substance from the storage chamber to the inhalation passage, the metering member having a metering surface which is indented to provide at least one dispensing cup and being moveable between a first position in which a dispensing cup is presented to the storage chamber to receive a dose of the substance and a second position in which a dose of the substance is presented to the inhalation passage in a dispensing cup which is upwardly open in use, the body comprising a seat having an annular contact surface making sliding contact with the metering surface, the contact surface being frusto-conical in shape so as to define a socket within which the metering member is journalled for rotation between its first and second positions.

Preferably, biassing means are provided to resiliently bias the metering member into contact with the seat.

In such an inhaler, the metering member preferably comprises a frusto-conical wall containing the dispensing cup or cups, the longitudinal axis of the frusto-conical wall lying, when the inhaler is held in its normal in-use position, between vertical and an angle of 60° to the vertical.

This inhaler may additionally comprise cup clearing means for ensuring that the or each dispensing cup is substantially free from the substance before being presented to the storage chamber. The cup clearing means may comprise means for moving the or each dispensing cup into a position from which, in normal use of the inhaler, any of the substance remaining in the dispensing cup would tend to fall, under the influence of gravity, out of the cup, after a dose of the substance has been presented in the cup to the inhalation passage and before that cup is again presented to the storage chamber. Alternatively or additionally, the cup clearing means may comprise an inhalation passage so formed that the dose of the substance presented to the inhalation passage is subjected to substantially the entire airflow through the inhalation passage when air is drawn into the inhaler in use, or resilient wiping means for dislodging any residual substance from the or each cup after a dose of the substance has been presented therein to the inhalation passage and before that cup is again presented to the storage compartment.

BRIEF DESCRIPTION OF THE DRAWINGS

The invention is exemplified in the accompanying drawings, in which.

DETAILED DESCRIPTION OF THE DRAWINGS

Figure 1:
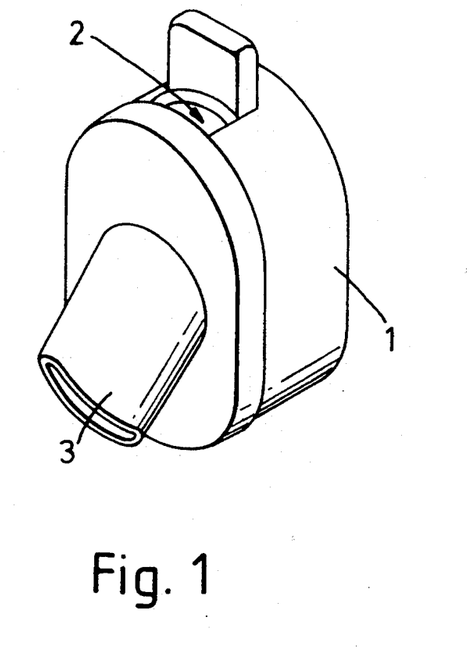
FIG. 1 is a general perspective view of an inhaler of the invention.
Figure 2:
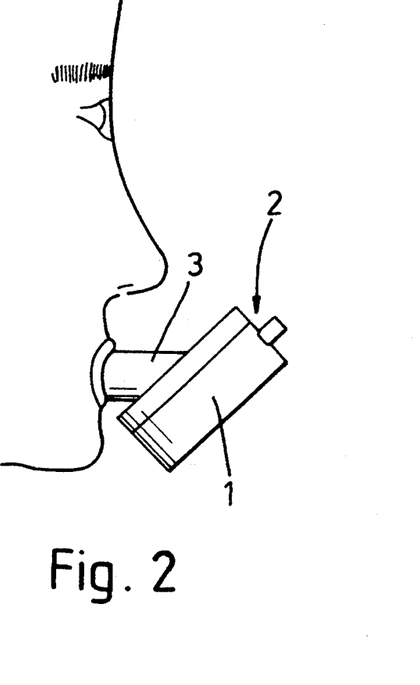
FIG. 2 is a side view of the inhaler in use.

As shown in the external views of FIGS. 1 and 2, the inhaler comprises a housing 1 which is provided with an air intake 2. A tubular mouthpiece 3 projects from the housing.

Referring to FIGS. 3 to 6, the housing contains an internal body 4 which, on its side remote from the mouthpiece 3, contains a recess 5 that provides a seat for a metering member 6 which is rotatable about its axis in the recess. The metering member includes a portion having a frusto-conical metering surface 7 which includes a series of circumferentially arranged cup-like metering depressions 8. The recess 5 provides a seat of corresponding frusto-conical shape, the angular tolerance and circumferential form of the metering surface and of the seat being carefully monitored in manufacture to ensure a close sliding contact between the two mating faces.

The opposite side of the body 4 includes a storage chamber 10 for a drug in the form of a micronised powder, the chamber 10 being arranged to register with one of the depressions 8. A second, outer chamber 11 surrounds the storage chamber 10 for containing a moisture absorbing material such as silica gel granules. The second chamber 11 is open to the depressions 8 on both sides of the depression which is currently in register with the storage chamber 10, but the silica gel is prevented from migrating into the depressions by a shaped filter membrane 12. The same side of the body 4 further contains an inhalation passage 15 and a waste chamber 16, both of which register with one of the depressions 8. The inhalation passage 15 has a smooth internal contour and registers with both the air inlet 2 and the mouthpiece 3. The air inlet 2 contains a filter membrane 17 for removing any contaminating particles that may be drawn into the inlet. The waste chamber 16 contains a brush, a piece of sponge rubber or other flexible wiping element 18 which projects into the corresponding depression 8 to make wiping contact with the walls of the depression.

Figure 3:
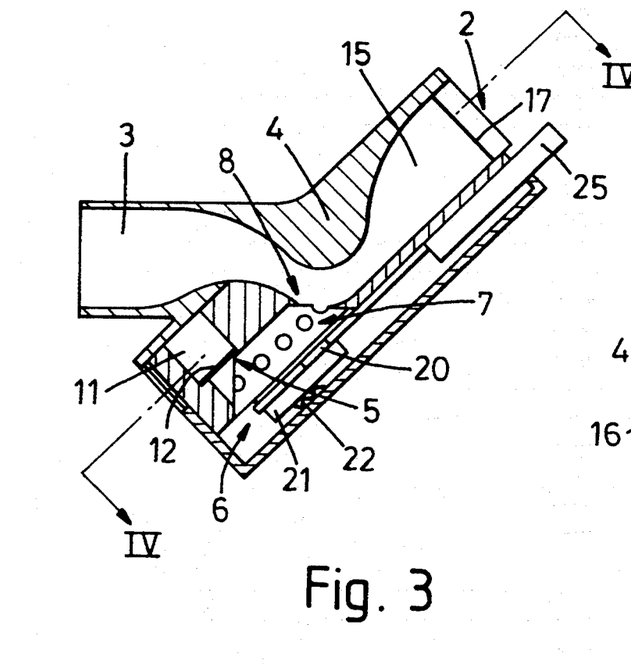
FIG. 3 is a longitudinal section through the inhaler.
Figure 4:
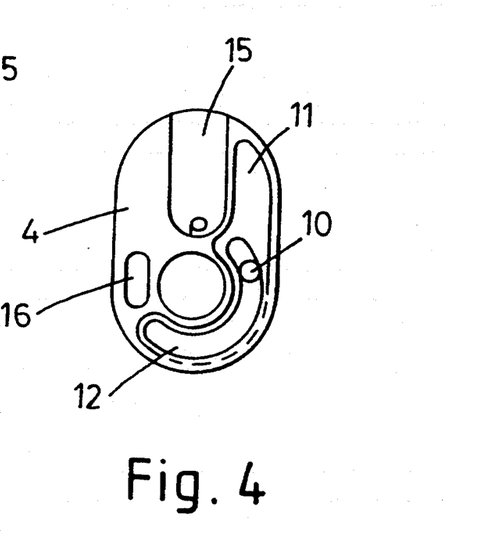
FIG. 4 is section IV—IV of FIG. 3.
Figure 5:
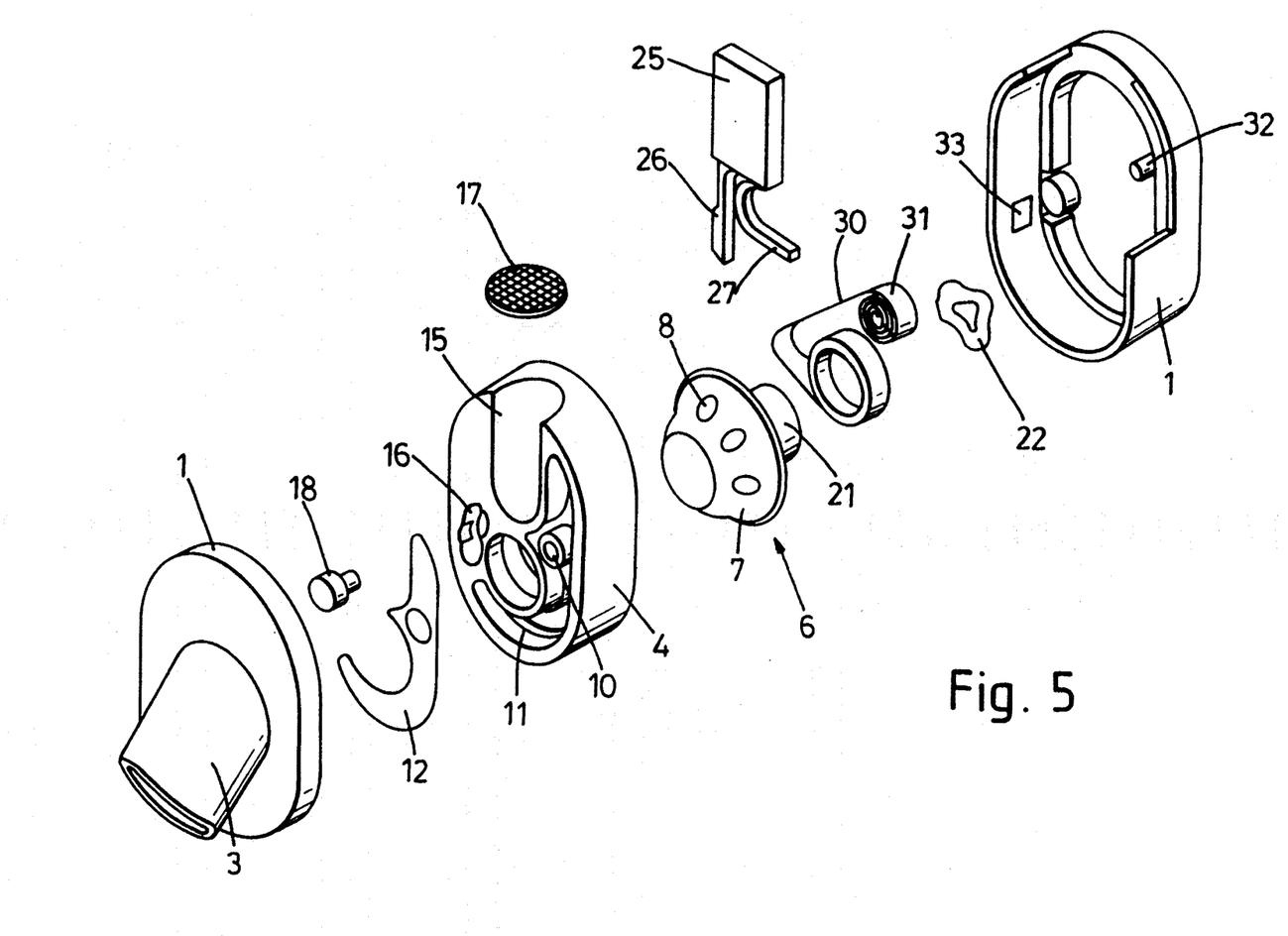
FIGS. 5 and 6 are exploded perspective views of the inhaler viewed from opposite ends.
Figure 6:
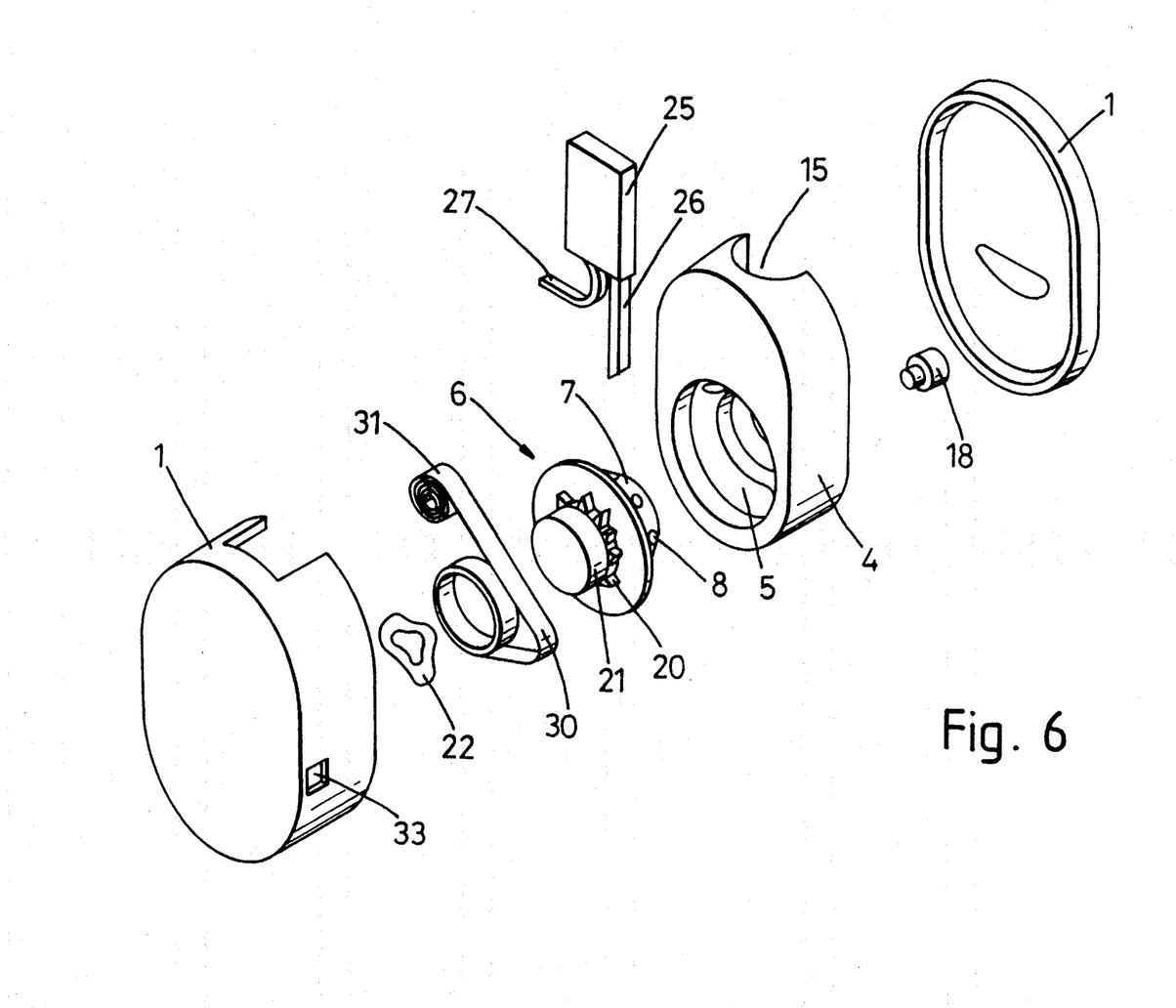
Figures 7A, 7B:
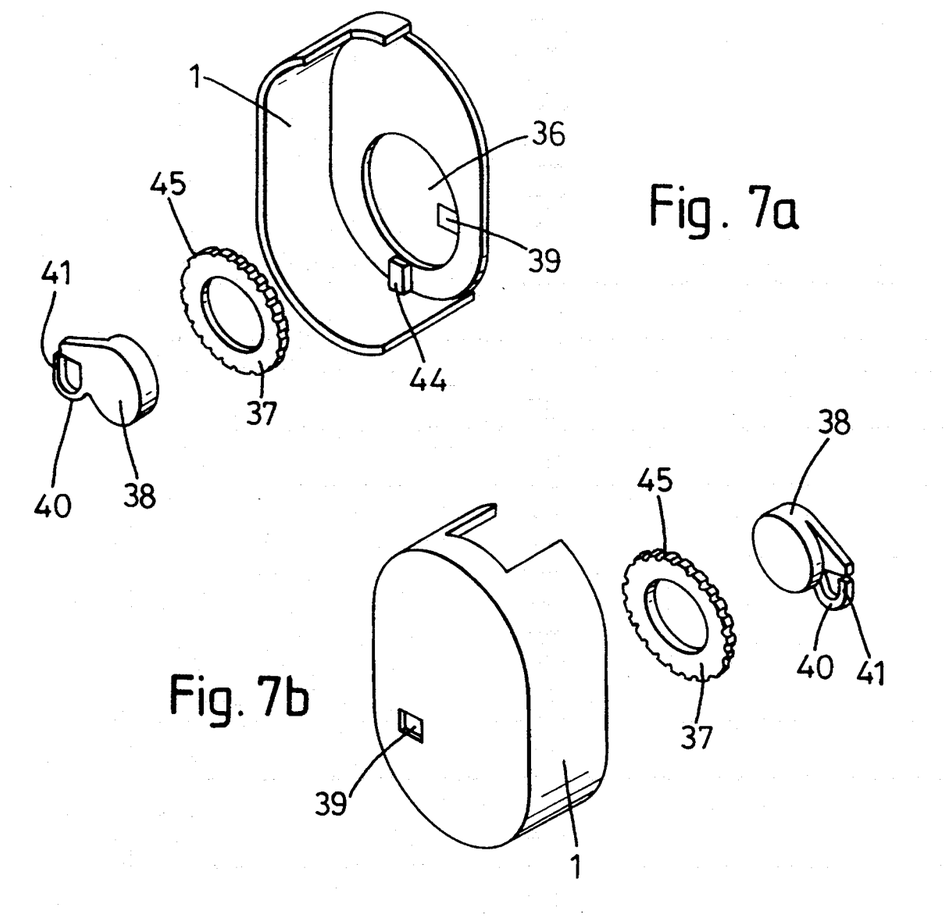
FIGS. 7a and 7b are exploded perspective views of the counter mechanism of the inhaler, again viewed from opposite ends.
Figure 8A:
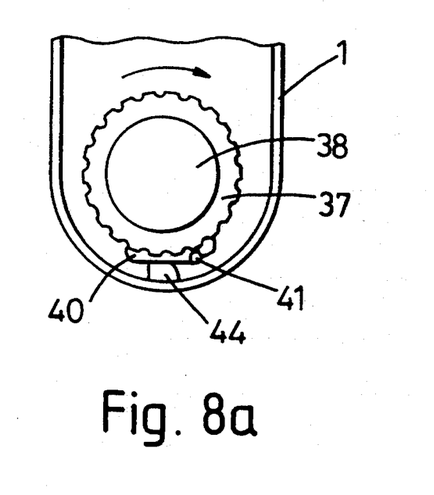
FIGS. 8a and 8b show the assembled counter mechanism viewed from opposite ends.
Figure 8B:
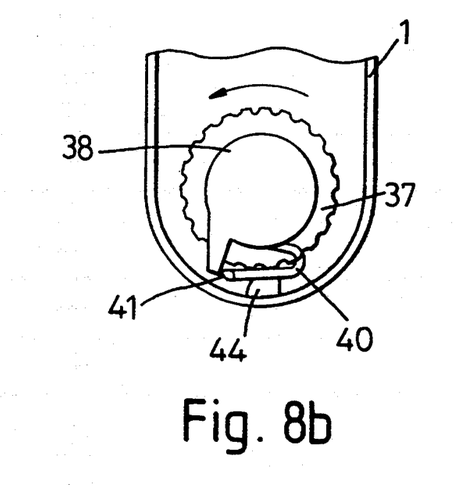

Referring more particularly to the inhalation passage 15, it can be seen from FIG. 3 that, when the inhaler is in use, the inhalation passage 15 extends in a downwards direction from the air intake 2, at least to the position where the dispensing cup 8 is presented to the inhalation passage. The width of the inhalation passage 15 is relatively large at the air intake, relatively small in the region of the dispensing cup and relatively large again at the mouthpiece 3. The inhalation passage includes a first relatively more-inclined portion extending generally downwardly from the air intake 2 to the dispensing cup 8 and a second relatively less-inclined portion extending from the dispensing cup 8 to the mouthpiece 3. Dispensing cup 8 is situated on the outside of the bend linking these two portions of the inhalation passage. Opposite the dispensing cup, the wall of the inhalation passage bulges across the inhalation passage towards a dispensing cup to create a restricted passageway in the region of the dispensing cup. In this region, the shape of the inhalation passage results in the air being both accelerated and directed towards the dispensing cup so that there is a highly efficient pick-up of material from the cup.

The frusto-conical head of the metering member 6 is secured to a co-axial circular ratchet formation 20 followed by a drum 21. A spring washer 22 acts between an end face of the drum 21 and the housing 1 to urge the metering member 6 against its seat in the recess 5. An indexing button 25 projects from the housing 1 adjacent to the inlet 2 and is secured to an integral indexing finger 26 for engagement with the ratchet formation 20. A spring finger 27, again integral with the button 25, projects transversely of the indexing finger 26 to engage the internal body 4 and thus urge the button to project from the housing 1.

A tape 30 is wound into a roll 31 which is freely rotatable on a pin 32 projecting from the inside of the housing 1. The leading end of the tape 30 is secured to the drum 21, onto which it is wound from the roll 30 upon rotation of the metering member 6. The tape 30 is routed past a window 33 in the housing 1 through which a contiguous series of numbers or other information carried on the tape is displayed.

In use, the inhaler will normally be supplied as a sealed unit with the storage chamber 10 pre-filled with medicament or other substance in a dry, finely divided form. With the button 25 uppermost, the depression 8 which is in register with the storage chamber 10 will fill with a fixed volume of the medicament. With the inhaler held in one hand the mouthpiece 3 is inserted into the mouth as shown in FIG. 2 and the button 25 is depressed using the index finger so that the indexing element 26 causes the metering member 6 to rotate by one position, thus bringing the next, empty depression 8 into register with the storage chamber 10. At the same time a filled depression comes into register with the inhalation passage 15. Thus, when air is drawn through the inhalation passage 15 via the mouthpiece 3, the internal contours of the inhalation passage causes the air to impinge on the material still held in the depression 8, causing the powder to be mixed into the air flow and, after passing through the mouthpiece 3, enter the mouth and air passages of the user.

It should be noted that the powder in the depression 8 is subjected to the entire airflow through the inhalation passage 15, from the air intake 2 to the mouthpiece 3, which enables the user more readily to achieve a full dose, and also promotes substantially complete removal of the powder from the depression 8.

As the depressions travel around the axis of the metering member with successive indexing movements of the button 25, they move past the wiping element 18 so that any residue of powder remaining in the depression is dislodged therefrom to fall into the waste chamber 16. Further travel of the depression causes it to move in register with the drying chamber 11 so that the silica gel can absorb any moisture from the depression before it comes into register with the storage chamber 10 to be refilled with medicament. The filled depressions may also move in register with the drying chamber 12 to reduce the possibility of moisture migrating from the inhalation passage 15 to the storage chamber 10. This may additionally ensure that the medicament remains dry, thereby ensuring that the vast majority of the medicament can be easily removed from the depression into the inhaled airflow.

It is important that the movement of a dose of powder to the dispensing position in the inhalation passage 15 is effected in such fashion as to maintain good sealing of the powder in the storage chamber 10, so that the integrity of the powder is preserved. This is facilitated by the provision of the frusto-conical shape of the metering surface 7 and of the seat for it provided by the recess 5; such a shape makes it possible to achieve a good seal between the metering surface 7 and its seat with less demanding tolerances than are feasible when other shapes are used. Providing that the angular tolerance is maintained (which is relatively simple), other manufacturing tolerances are accommodated by the self-sealing arrangements of the metering surface 7 and the seat provided by the recess 5.

In normal use of the inhaler, repeated indexing of the metering member 6 will not deposit multiple doses of the substance into the inhalation passage. Instead, each dose will simply be carried round in the depression 8 until it is discarded into the waste chamber 16.

Each time the metering member is indexed, new information is carried into the window 33 by the tape 30. This information could simply be a number indicating how many doses have been used, or how many remain to be used, or both. The window could also display other information such as the time when the next dose should be taken.

Normally, the device will be disposed of once the intended number of doses has been used. It is, however, envisaged that the internal body 4 could contain a replaceable cartridge containing a fresh supply of medicament and possibly also fresh silica gel, new filters 12 and/or 17, and a fresh tape 31. This tape could be partially wound onto a replaceable drum 21 which engages the frusto-conical metering head 6.

A modified counting arrangement is shown in FIGS. 7a, 7b and 8a, 8b. The housing 1 contains a circular internal recess 36 which receives an outer ring 37 and an inner disc 38 which are arranged co-axially with the metering member 6. The disc 38 carries the units 0 to 9 at 36° intervals whereas the ring 37 is marked in multiples of tens at regular angular intervals. The tens and units are disposed so that they can both be displayed through a window 39 in the housing 1. The disc 38 is connected to, or driven by, the metering member 6 and carries an integral spring arm 40 which carries a pin 41 to act as a cam follower. Whenever the disc 38 completes one rotation, the arm 39 engages a cam 44 secured to the interior of the housing 1, which causes the cam follower 41 to engage in one of a series of notches 45 around the outer periphery of the ring 37. This, in turn, indexes the ring by one angular position on each rotation of the disc 38. The number displayed in the window 40 can thus be incremented from, say, 1 to 200 to count the number of doses used. Instead of a ring surrounding the disc 38, a second transparent disc could be disposed behind the disc 38 so that the units are visible through the second disc, which again carries multiples of tens.

I claim:

1. An inhaler for delivering a substance in a finely divided form, comprising a body defining a storage chamber for the substance to be delivered and further defining an inhalation passage through which air is drawn via a mouthpiece; a metering member having a metering surface which is indented to provide at least one dispensing cup; and means for moving the metering member between a first position in which a dispensing cup is presented to the storage chamber to receive a volumetric dose of the substance and a second position in which a volumetric dose of the substance is presented to the inhalation passage in an upwardly open dispensing cup and in which, in normal use of the inhaler, at least a major proportion of the substance in the dispensing cup is retained in the cup by the influence of gravity before air is drawn through the inhalation passage; said means for moving comprising means for moving the or each dispensing cup into a third position different from said first and second positions from which, in normal use of the inhaler, any of the substance remaining in the dispensing cup would tend to fall out of the cup, under the influence of gravity, after a dose of the substance has been presented in the cup to the inhalation passage and before that cup is again presented to the storage chamber, to ensure that the or each dispensing cup is substantially free from the substance before being presented to the storage chamber.

2. An inhaler according to claim 1, in which the inhalation passage is so formed that the dose of the substance presented to the inhalation passage is subjected to substantially the entire airflow through the inhalation passage when air is drawn through the mouthpiece.

3. An inhaler according to claim 1, comprising resilient wiping means for dislodging any residual substance from the or each cup after a dose of the substance has been presented therein to the inhalation passage and before that cup is again presented to the storage chamber.

4. An inhaler according to claim 1, in which the metering member is resiliently biased into contact with a seat and said means for moving is adapted to move the metering member while the metering member is in contact with the seat.

5. An inhaler according to claim 4, in which said means for moving is adapted to rotate the metering member while the metering member is in contact with the seat.

6. An inhaler according to claim 1, in which the metering member comprises a frusto-conical wall containing the dispensing cup or cups.

7. An inhaler according to claim 6, in which the longitudinal axis of the frusto-conical wall lies, when the inhaler is held in its normal in-use position, between vertical and an angle of 60° to the vertical.

8. An inhaler according to claim 6, in which the body comprises a seat having an annular contact surface making sliding contact with the frusto-conical wall of the metering member, the contact surface being correspondingly frusto-conical in shape so as to define a socket within which the metering member is journalled for rotation between its first and second positions.

9. An inhaler according to claim 8, in which the metering member is resiliently biased into contact with the seat.

10. An inhaler according to claim 1 including a chamber containing moisture-absorbent material, the means for moving being adapted to move the or each dispensing cup into register with said chamber after a dose of the substance has been presented to the inhalation passage and before that cup is again presented to the storage chamber.

11. An inhaler according to claim 1, including a chamber containing moisture-absorbent material, the means for moving being adapted to move the or each dispensing cup into register with said chamber after being presented to the storage chamber and before a dose of the substance has been presented to the inhalation passage.

12. An inhaler according to claim 1, including a display mechanism which is indexed in association with the metering member to display an item of information to the user.

* * * * *

Disclaimer

5,437,270—Philip Wilson Braithwaite, United Kingdom, POWER INHALER HAVING A MUILTI-POSI-TIONED METERING CUP, Patent dated Aug. 1, 1995. Disclaimer filed June 2, 2011, by the Assignee, Innovata Biomed Limited.

Hereby enters this disclaimer to claims 1-12, of said patent.

(*Official Gazette January 24, 2012*)